United States Patent
Rees et al.

[11] Patent Number: 6,013,605
[45] Date of Patent: Jan. 11, 2000

[54] SYNERGISTIC HERBICIDAL MIXTURES

[75] Inventors: Richard Rees, Pensacola, Fla.; Jürgen Bohner; Eberhard Richter, both of Berlin, Germany

[73] Assignee: Hoechst Scharing AgrEvo GmbH, Berlin, Germany

[21] Appl. No.: 09/068,137

[22] PCT Filed: Nov. 12, 1996

[86] PCT No.: PCT/EP96/04935

§ 371 Date: May 1, 1998

§ 102(e) Date: May 1, 1998

[87] PCT Pub. No.: WO97/17852

PCT Pub. Date: May 22, 1997

[30] Foreign Application Priority Data

Nov. 15, 1995 [DE] Germany .................. 195 44 393

[51] Int. Cl.⁷ .................................................. A01N 43/90
[52] U.S. Cl. ............................................ 504/221; 546/112
[58] Field of Search ............................ 504/221; 546/112

[56] References Cited

FOREIGN PATENT DOCUMENTS

0542388 A1  5/1993  European Pat. Off. .
WO 94/08999  4/1994  WIPO .

*Primary Examiner*—Zinna Northington Davis
*Attorney, Agent, or Firm*—Frommer Lawrence & Haug LLP

[57] ABSTRACT

A synergistically active herbicidal composition which comprises, as active components, a mixture of 1-(3-chloro-4,5,6,7-tetrahydropyrazolo-[1,5-a]-pyridin-2-yl)-5-(methylpropargylamino)-4-pyrazolylcarbonitrile [Component (A)] and a herbicide selected from the group consisting of bentazone, molinate, daimuron, thiobencarb, butachlor, pretilachlor, dimepiperate, fenoxaprop-ethyl, clomeprop, cinmethylin, bromobutide, quinclorac, mefenacet, pyrazosulfuron-ethyl, esprocarb, cinosulfuron, thenylchlor, cumyluron, MK 243, naproanilide, anilofos, benfuresate, bifenox, CH-900, MCPA, nitrofen, oxadiazon, pendimethalin, simetryn, sulcotrione (ICIA0051), trifluralin, piperophos, pyributicarb, ethoxysulfuron, bensulfuronmethyl, pyrazolate, pyrazoxyfen, benzofenap, cyclosulfamuron, cyhalofop-butyl, NBA-061, azimsulfuron, propanil or imazosulfuron [Component (B)] and which are suitable for controlling undesirable plants in rice cultivation.

6 Claims, No Drawings

SYNERGISTIC HERBICIDAL MIXTURES

This application is a 371 of PCT/EP96/04935, filed on Nov. 12, 1996.

The invention relates to novel mixtures of 1-(3-chloro-4,5,6,7-tetrahydropyrazolo-[1,5-a]-pyridin-2-yl)-5-(methylpropargylamino)-4-pyrazolylcarbonitrile and other herbicides, and to their use for controlling weeds in agricultural crops.

The herbicidal action of 1-(3-chloro-4,5,6,7-tetrahydropyrazolo-[1,5-a]-pyridin-2-yl)-5-(methylpropargylamino)-4-pyrazolylcarbonitrile has already been disclosed (DE OS 43 15 330). Furthermore, it is known that the use of mixtures of active substances can result in specific advantages, especially since the use of the individual active substances is unsatisfactory in most cases.

It has now been found that herbicidal compositions which comprise, as active components, a mixture of 1-(3-chloro-4,5,6,7-tetrahydropyrazolo-[1,5-a]-pyridin-2-yl)-5-(methylpropargylamino)-4-pyrazolylcarbonitrile [Component (A)] and another herbicide selected from the group consisting of bentazone, molinate, daimuron, thiobencarb, butachlor, pretilachlor, dimepiperate, fenoxaprop-ethyl, clomeprop, cinmethylin, bromobutide, quinclorac, mefenacet, pyrazosulfuron-ethyl, esprocarb, cinosulfuron, thenylchlor, cumyluron, MK 243, naproanilide, anilofos, benfuresate, bifenox, CH-900, MCPA, nitrofen, oxadiazon, pendimethalin, simetryn, sulcotrione (ICIA0051), trifluralin, piperophos, pyributicarb, ethoxysulfuron, bensulfuronmethyl, pyrazolate, pyrazoxyfen, benzofenap, cyclosulfamuron, cyhalofop-butyl, NBA-061, azimsulfuron, propanil or imazosulfuron [Component (B)] exhibit an especially high herbicidal activity without losing the selective properties relative to agricultural crops such as rice and which in some cases even decidedly improve crop compatibility.

With the exception of cumyluron and NBA-061, the active substances of Component (B) are known, for example, from The Pesticidal Manual, 10th Edition (1994), Brit. Crop Prot. Council, London, and The Royal Soc. of Chem., Cambridge. Cumyluron itself has been described, inter alia, in Agrochem. Jpn., 63, 18–19, 1993 (Konnai et al.) and NBA-061 in DE 504059, EP 612735 and EP 726259.

Surprisingly, the herbicidal activity of the active substance combinations according to the invention by far exceeds the activity of the individual components and also the total of the individual components. Thus, a synergistic effect is present.

For example, the active substance combinations according to the invention can be used for controlling the following plants:

dicotyledon weeds of the genera Lindernia, Rotala, Mimosa, Heteranthera, Sinapis, Galium, Stellaria, Matricaria, Galinsoga, Chenopodium, Brassica, Urtica, Senecio, Amaranthus, Portulaca, Xanthium, Convolvulus, Ipomea, Polygonum, Sesbania, Cirsium, Carduus, Sonchus, Solanum, Lamium, Veronica, Abutilon, Datura and Viola, and monocotyledon weeds of the genera Alisma, Avena, Alopecurus, Echinochloa, Setaria, Scirpus, Panicum, Digitaria, Poa, Eleusine, Brachiaria, Lolium, Bromus, Cyperus, Agropyron, Sagittaria, Monochoria, Fimbristylis, Eleocharis, Ischaemum, Potamogeton, Eichhornia and Apera.

The mixtures according to the invention are employed post-emergence by direct application, for example by spraying them onto the plants, or else pre-emergence by direct application into the paddy water, or by spraying. Selective application is possible in a series of crop plantings, of which rice is preferred. The rate of application is between 0.001 and 5 kg/ha for the total of the components in the mixture, depending on the intended purpose.

The weight ratio of Component (A) to Component (B) in the mixture is between 1:0.1 and 1:100, preferably 1:0.5 and 1:50.

If desired, the compositions according to the invention can also be used in the form of a mixture with other active substances, for example other crop protection chemicals or pesticides, depending on the intended purpose.

Moreover, the intensity and speed of action can be enhanced for example by activity-promoting additives such as organic solvents, wetting agents and oils. Such additives may therefore allow the dosage rate of active substance to be reduced even further.

It is expedient to employ the compositions characterized in the form of preparations such as powders, materials for spreading, granules, solutions, emulsions or suspensions with an addition of liquid and/or solid carriers or diluents and, if appropriate, tackifiers, wetting agents, emulsifiers and/or dispersants.

Examples of suitable liquid carriers are aliphatic and aromatic hydrocarbons such as toluene, xylene, or else cyclohexanone, isophorone, dimethyl sulfoxide, dimethylformamide, and furthermore mineral oil fractions and vegetable oils.

Suitable solid carriers are minerals, for example bentonite, silica gel, talc, kaolin, attapulgite, limestone and products of vegetable origin, for example meals.

Examples of surfactants to be mentioned are calcium ligninsulfonate, polyethylene alkylphenyl ethers, naphthalenesulfonic acid and its salts, phenolsulfonic acids and their salts, formaldehyde condensates, fatty alcohol sulfonates and substituted benzenesulfonic acids and their salts.

The amount of the active substances in the various preparations can be varied within wide limits. For example, the compositions comprise approximately 10 to 90 percent by weight of active substances, approximately 90 to 10 percent by weight of liquid or solid carriers and, if appropriate, up to 20 percent by weight of surfactants.

The compositions can be applied in the customary manner, for example using water as carrier at rates of approximately 100 to 1000 liters of spray mixture per ha. Application of the compositions by the so-called low-volume and ultra-low-volume methods (ULV) is equally possible, as is their application in the form of granules and microgranules.

These preparations can be prepared in a manner known per se, for example by grinding or mixing processes. If desired, preparations of the individual components can also be mixed only just before they are used, as is the case, for example, when preparing a tank mix under realistic conditions.

The examples which follow are intended to illustrate the use of the compositions according to the invention.

The synergistic effect was calculated as described by S. R. Colby in "Calculating Synergistic and Antagonistic Responses of Herbicide Combinations" Weeds 15/1 (1967), pages 20 to 22.

The following formula was used for this purpose:

$$E = X + Y - \frac{XY}{100}$$

where
X=herbicidal activity (%) when applying substance A at p g/ha
Y=herbicidal activity (%) when applying substance B at q g/ha and
E=herbicidal activity (%) to be expected when the application of substances A+B at p+q g/ha amount to an additive effect.

If the observed value exceeded the value E calculated using Colby's formula, the combination had a synergistic effect.

DESCRIPTION OF METHODS

Square dishes with a side length of 13.5 cm and a height of 8.0 cm are filled with 900 ml of soil mixture. The following species are sown or planted in the dishes following a set routine:

| Species | Planting rate | BAYER code |
|---|---|---|
| Orysa sativa | 4 seeds | ORYSW |
| Oryza sativa (depth 3 cm) | 3 plants | ORYSA |
| Oryza sativa (depth 1 cm) | 2 plants | ORYSP |
| Echinocloa crus-galli | approx. 20 seeds | ECHCG |
| Echinocloa crus-galli (E) | approx. 20 seeds | ECHCG (E. = Europe) |
| Echinocloa crus galli (US) | approx. 20 seeds | ECHCG (US = U.S.A.) |
| Cyperus serotinus | 3 tubers | CYPSE |
| Scirpus juncoides | approx. 30 seeds | SCPJU |
| Sagittaria pygmaea | 3 tubers | SAGPY |
| Monochoria vaginalis | 4 nodes | MOOVA |
| Cyperus difformis | approx. 80 seeds | CYPDI |
| Paspalum distichum | 4 nodes | PASDS |

During the entire experimental period, the dishes remain in the greenhouse at a temperature between 25° C. during the day and 20° C. during the night. The atmospheric humidity is between 60 and 80%. During a 14-hour photo period, the plants receive at least 10,000 lux.

Depending on the efficiency, the test substances are tested at three different concentrations.

For the pre-emergence treatment, the test substances are applied to the sown plants by spraying in such a way that those dosages per hectare which are given in the tables result (converted).

For post-emergence treatment, ECHCG, SCPJU, MOOVA and SAGPY are sown into the first dish, and CYPDI and CYPSE and the pregerminated sown rice seeds are placed into the second dish. After one day, the dishes are covered with transparent film to avoid desiccation. Three days prior to application, batches of three rice plants in the 2.5-leaf stage are planted in the second dish at a depth of 3 cm and 1 cm, respectively. Once Echinochloa crus-galli is in the 1.0-leaf stage, the active substance, or mixture, is applied. The water level is raised to 1–2 cm. The test substances are applied by pipetting onto a water surface area of approximately 170 cm$^2$ so that the dosages per hectare which are given in the tables is result (converted).

EXAMPLE 1

Mixtures of (A) with Bifenox (B1)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5/25/50 g/ha and (B1) at rates of 50/100/200 g/ha.

Synergistic effects were observed with ECHCG (E), CYPSE, MOOVA and SCPJU, as can be seen from Table 1 below.

TABLE 1

| A/B | Component/species Quantity (g/ha) | ECHCG (E) Activ. (%) | Colby (%) | CYPSE Activ. (%) | Colby (%) | MOOVA Activ. (%) | Colby (%) | SCPJU Activ. (%) | Colby (%) |
|---|---|---|---|---|---|---|---|---|---|
| A | 12.5 | 60 | | 35 | | 90 | | 20 | |
| | 25 | 80 | | 40 | | 95 | | 30 | |
| | 50 | 95 | | 80 | | 100 | | 65 | |
| B1 | 50 | 0 | | 0 | | 65 | | 0 | |
| | 100 | 0 | | 0 | | 70 | | 0 | |
| | 200 | 0 | | 0 | | 75 | | 0 | |
| A + B1 | 12.5 + 50 | 60 | 60.0 | 35 | 35.0 | 95 | 96.5 | 25 | 20.0 |
| | 25 + 50 | 75 | 80.0 | 60 | 40.0 | 100 | 98.3 | 40 | 30.0 |
| | 50 + 50 | 98 | 95.0 | 75 | 80.0 | 100 | 100.0 | 65 | 65.0 |
| | 12.5 + 100 | 65 | 60.0 | 40 | 35.0 | 98 | 97.0 | 30 | 20.0 |
| | 25 + 100 | 85 | 80.0 | 60 | 40.0 | 100 | 98.5 | 60 | 30.0 |
| | 50 + 100 | 98 | 95.0 | 80 | 80.0 | 100 | 100.0 | 70 | 65.0 |
| | 12.5 + 200 | 60 | 60.0 | 35 | 35.0 | 100 | 97.5 | 30 | 20.0 |
| | 25 + 200 | 90 | 80.0 | 40 | 40.0 | 100 | 98.8 | 70 | 30.0 |
| | 50 + 200 | 95 | 95.0 | 85 | 80.0 | 100 | 100.0 | 75 | 65.0 |

EXAMPLE 2

Mixtures of (A) with CH-900 (B2)

For the experiment, 1-(3-chloro-4,5,6,7-tetrahydropyrazolo-[1,5-a]-pyridin2-yl)-5 (methylpropargylamino)-4-pyrazolylcarbonitrile (A) was applied at rates of 12.5/25/50 g/ha and (B2) at rates of 12.5/25/50 g/ha.

Synergistic effects were observed with ECHCG (E), SAGPY, SCPJU and CYPDI, as can be seen from Table 2 below.

TABLE 2

| A/B | Component/species Quantity (g/ha) | ECHCG (E) Activ. (%) | Colby (%) | SAGPY Activ. (%) | Colby (%) | SCPJU Activ. (%) | Colby (%) | CYPDI Activ. (%) | Colby (%) |
|---|---|---|---|---|---|---|---|---|---|
| A | 12.5 | 10 | | 10 | | 20 | | 0 | |
|   | 25 | 75 | | 65 | | 40 | | 20 | |
|   | 50 | 90 | | 70 | | 60 | | 30 | |
| B2 | 12.5 | 40 | | 10 | | 0 | | 0 | |
|   | 25 | 70 | | 20 | | 25 | | 95 | |
|   | 50 | 98 | | 25 | | 50 | | 98 | |
| A + B2 | 12.5 + 12.5 | 20 | 46.0 | 10 | 19.0 | 20 | 20.0 | 40 | 0.0 |
|   | 25 + 12.5 | 40 | 85.0 | 60 | 68.5 | 65 | 40.0 | 60 | 20.0 |
|   | 50 + 12.5 | 90 | 94.0 | 70 | 73.0 | 70 | 60.00 | 100 | 30.0 |
|   | 12.5 + 25 | 60 | 73.0 | 30 | 28.0 | 60 | 40.0 | 40 | 95.0 |
|   | 25 + 25 | 65 | 92.5 | 40 | 72.0 | 70 | 55.0 | 80 | 96.0 |
|   | 50 + 25 | 98 | 97.0 | 100 | 76.0 | 75 | 70.00 | 95 | 96.5 |
|   | 12.5 + 50 | 100 | 98.2 | 40 | 32.5 | 60 | 60.0 | 90 | 98.0 |
|   | 25 + 50 | 100 | 99.5 | 50 | 73.8 | 65 | 70.0 | 100 | 98.4 |
|   | 50 + 50 | 100 | 99.8 | 90 | 77.5 | 75 | 80.00 | 100 | 98.6 |

EXAMPLE 3

Mixtures of (A) with MCPA (B3)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5/25/50 g/ha and (B3) at rates of 50/100/200 g/ha.

Synergistic effects were observed with the two ECHCG species, CYPSE, SCPJU and CYPDI, as can be seen from Table 3 below.

EXAMPLE 4

Mixtures of (A) with Nitrofen (B4)

For the experiment, 1-(3-chloro-4,5,6,7-tetrahydropyrazolo-[1,5-a]-pyridin-2-yl)-5-methylpropargylamino)-4-pyrazolylcarbonitrile (A) was applied at rates of 12.5/25/50 g/ha and (B4) at rates of 25/50/200 g/ha.

Synergistic effects were observed with ECHCG, SAGPY, SCPJU and CYPDI, as can be seen from Table 4 below.

TABLE 3

| A/B | Component/species Quantity (g/ha) | ECHCG (E) Activ. (%) | Colby (%) | ECHCG (US) Activ. (%) | Colby (%) | CYPSE Activ. (%) | Colby (%) | SCPJU Activ. (%) | Colby (%) | CYPDI Activ. (%) | Colby (%) |
|---|---|---|---|---|---|---|---|---|---|---|---|
| A | 12.5 | 75 | | 50 | | 30 | | 10 | | 5 | |
|   | 25 | 95 | | 90 | | 35 | | 40 | | 20 | |
|   | 50 | 100 | | 100 | | 85 | | 75 | | 25 | |
| B3 | 50 | 0 | | 0 | | 30 | | 0 | | 0 | |
|   | 100 | 20 | | 20 | | 40 | | 10 | | 10 | |
|   | 200 | 30 | | 60 | | 60 | | 40 | | 100 | |
| A + B3 | 12.5 + 50 | 80 | 75.0 | 75 | 50.0 | 45 | 51.0 | 20 | 10.0 | 10 | 5.0 |
|   | 25 + 50 | 98 | 95.0 | 95 | 90.0 | 75 | 54.5 | 45 | 40.0 | 20 | 20.0 |
|   | 50 + 50 | 100 | 100.0 | 100 | 100.0 | 90 | 89.5 | 80 | 75.0 | 30 | 25.0 |
|   | 12.5 + 100 | 85 | 80.0 | 75 | 60.0 | 60 | 58.0 | 25 | 19.0 | 70 | 14.5 |
|   | 25 + 100 | 95 | 96.0 | 95 | 92.0 | 65 | 61.0 | 60 | 46.0 | 80 | 28.0 |
|   | 50 + 100 | 100 | 100.0 | 100 | 100.0 | 90 | 91.0 | 90 | 77.5 | 95 | 32.5 |
|   | 12.5 + 200 | 85 | 82.5 | 75 | 80.0 | 75 | 72.0 | 75 | 46.0 | 90 | 100.0 |
|   | 25 + 200 | 98 | 96.5 | 95 | 96.0 | 80 | 74.0 | 84 | 64.0 | 95 | 100.0 |
|   | 50 + 200 | 100 | 100.0 | 100 | 100.0 | 95 | 94.0 | 95 | 85.0 | 100 | 100.0 |

TABLE 4

| A/B | Component/species Quantity (g/ha) | ECHCG Activ. (%) | ECHCG Colby (%) | SAGPY Activ. (%) | SAGPY Colby (%) | SCPJU Activ. (%) | SCPJU Colby (%) | CYPDI Activ. (%) | CYPDI Colby (%) |
|---|---|---|---|---|---|---|---|---|---|
| A | 12.5 | 10 | | 10 | | 15 | | 0 | |
| | 25 | 20 | | 20 | | 30 | | 10 | |
| | 50 | 90 | | 60 | | 60 | | 30 | |
| B4 | 25 | 0 | | 5 | | 0 | | 0 | |
| | 50 | 25 | | 10 | | 20 | | 20 | |
| | 100 | 80 | | 20 | | 30 | | 25 | |
| A + B4 | 12.5 + 25 | 40 | 10.0 | 10 | 14.5 | 20 | 15.0 | 20 | 0.0 |
| | 25 + 25 | 80 | 20.0 | 25 | 24.0 | 25 | 30.0 | 30 | 10.0 |
| | 50 + 25 | 85 | 90.0 | 65 | 62.0 | 60 | 60.0 | 60 | 30.0 |
| | 12.5 + 50 | 70 | 32.5 | 20 | 19.0 | 30 | 32.0 | 20 | 20.0 |
| | 25 + 50 | 65 | 40.0 | 25 | 28.0 | 40 | 44.0 | 75 | 28.0 |
| | 50 + 50 | 98 | 92.5 | 70 | 64.0 | 70 | 68.0 | 80 | 44.0 |
| | 12.5 + 200 | 75 | 82.0 | 30 | 28.0 | 40 | 40.5 | 20 | 25.0 |
| | 25 + 200 | 80 | 84.0 | 50 | 36.0 | 65 | 51.0 | 80 | 32.5 |
| | 50 + 200 | 90 | 98.0 | 70 | 68.0 | 75 | 72.0 | 90 | 47.5 |

EXAMPLE 5

Mixtures of (A) with Oxadiazon (B5)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5/25/50 g/ha and (B5) at rates of 125/250/500 g/ha.

Synergistic effects were observed with ECHCG (E), CYPSE, SAGPY and SCPJU, as can be seen from Table 5 below.

EXAMPLE 6

Mixtures of (A) with Pendimethalin (B6)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5/25/50 g/ha and (B6) at rates of 50/100/200 g/ha.

Synergistic effects were observed with ECHCG (US), CYPSE, SAGPY and CYPDI, as can be seen from Table 6 below.

TABLE 5

| A/B | Component/species Quantity (g/ha) | ECHCG (E) Activ. (%) | ECHCG (E) Colby (%) | CYPSE Activ. (%) | CYPSE Colby (%) | SAGPY Activ. (%) | SAGPY Colby (%) | SCPJU Activ. (%) | SCPJU Colby (%) |
|---|---|---|---|---|---|---|---|---|---|
| A | 12.5 | 60 | | 30 | | 10 | | 10 | |
| | 25 | 90 | | 45 | | 20 | | 40 | |
| | 50 | 100 | | 80 | | 85 | | 60 | |
| B5 | 125 | 90 | | 5 | | 0 | | 20 | |
| | 250 | 100 | | 10 | | 10 | | 30 | |
| | 500 | 100 | | 20 | | 20 | | 70 | |
| A + B5 | 12.5 + 125 | 98 | 96.0 | 35 | 33.5 | 10 | 10.0 | 30 | 28.0 |
| | 25 + 125 | 100 | 99.0 | 40 | 47.8 | 20 | 20.0 | 50 | 52.0 |
| | 50 + 125 | 100 | 100.0 | 90 | 81.0 | 85 | 85.0 | 80 | 68.0 |
| | 12.5 + 250 | 100 | 100.0 | 75 | 37.0 | 30 | 19.0 | 35 | 37.0 |
| | 25 + 250 | 100 | 100.0 | 85 | 50.5 | 35 | 28.0 | 50 | 58.0 |
| | 50 + 250 | 100 | 100.0 | 95 | 82.0 | 85 | 86.5 | 80 | 72.0 |
| | 12.5 + 500 | 100 | 100.0 | 75 | 44.0 | 70 | 28.0 | 70 | 73.0 |
| | 25 + 500 | 100 | 100.0 | 90 | 56.0 | 80 | 36.0 | 80 | 82.0 |
| | 50 + 500 | 100 | 100.0 | 95 | 84.0 | 90 | 88.0 | 90 | 88.0 |

TABLE 6

| A/B | Component/species Quantity (g/ha) | ECHCG (US) Activ. (%) | Colby (%) | CYPSE Activ. (%) | Colby (%) | SAGPY Activ. (%) | Colby (%) | CYPDI Activ. (%) | Colby (%) |
|---|---|---|---|---|---|---|---|---|---|
| A | 12.5 | 35 | | 30 | | 50 | | 0 | |
| | 25 | 80 | | 35 | | 55 | | 0 | |
| | 50 | 97 | | 80 | | 70 | | 90 | |
| B6 | 50 | 98 | | 0 | | 60 | | 30 | |
| | 100 | 99 | | 0 | | 25 | | 35 | |
| | 200 | 99 | | 0 | | 30 | | 70 | |
| A + B6 | 12.5 + 50 | 97 | 98.7 | 30 | 30.0 | 25 | 80.0 | 30 | 30.0 |
| | 25 + 50 | 98 | 99.6 | 50 | 35.0 | 50 | 82.0 | 45 | 30.0 |
| | 50 + 50 | 100 | 99.9 | 60 | 80.0 | 98 | 88.0 | 70 | 93.0 |
| | 12.5 + 100 | 100 | 99.4 | 45 | 30.0 | 25 | 62.5 | 50 | 35.0 |
| | 25 + 100 | 100 | 99.8 | 55 | 35.0 | 55 | 66.3 | 60 | 35.0 |
| | 50 + 100 | 100 | 100.0 | 75 | 80.0 | 90 | 77.5 | 75 | 93.5 |
| | 12.5 + 200 | 100 | 99.4 | 45 | 30.0 | 30 | 65.0 | 55 | 70.0 |
| | 25 + 200 | 100 | 99.8 | 70 | 35.0 | 55 | 68.5 | 65 | 70.0 |
| | 50 + 200 | 100 | 100.0 | 75 | 80.0 | 95 | 79.0 | 80 | 97.0 |

EXAMPLE 7

Mixtures of (A) with Simetryn (B7)

For the experiment, 1-(3-chloro-4,5,6,7-tetrahydropyrazolo-[1,5-a]-pyridin-2-yl)-5-(methylpropargytamino)-4-pyrazolylcarbonitrile (A) was applied at rates of 12.5/25/50 g/ha and (B7) at rates of 50/100/200 g/ha.

Synergistic effects were observed with CYPSE, SAGPY, SCPJU and CYPDI, as can be seen from Table 7 below.

EXAMPLE 8

Mixtures of (A) with Sulcotrione (B8)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5/25/50 g/ha and (B8) at rates of 25/50/100 g/ha.

Synergistic effects were observed with the two ECHCG species, SAGPY, SCPJU and CYPDI, as can be seen from Table 8 below.

TABLE 7

| A/B | Component/species Quantity (g/ha) | CYPSE Activ. (%) | Colby (%) | SAGPY Activ. (%) | Colby (%) | SCPJU Activ. (%) | Colby (%) | CYPDI Activ. (%) | Colby (%) |
|---|---|---|---|---|---|---|---|---|---|
| A | 12.5 | 20 | | 30 | | 20 | | 0 | |
| | 25 | 30 | | 40 | | 40 | | 10 | |
| | 50 | 70 | | 70 | | 60 | | 75 | |
| B7 | 50 | 0 | | 0 | | 0 | | 20 | |
| | 100 | 10 | | 0 | | 0 | | 95 | |
| | 200 | 20 | | 20 | | 10 | | 100 | |
| A + B7 | 12.5 + 50 | 30 | 20.0 | 65 | 30.0 | 20 | 20.0 | 90 | 20.0 |
| | 25 + 50 | 40 | 30.0 | 70 | 40.0 | 40 | 40.0 | 95 | 28.0 |
| | 50 + 50 | 75 | 70.0 | 75 | 70.0 | 65 | 60.0 | 100 | 80.0 |
| | 12.5 + 100 | 30 | 28.0 | 60 | 30.0 | 20 | 20.0 | 100 | 95.0 |
| | 25 + 100 | 85 | 37.0 | 75 | 40.0 | 45 | 40.0 | 100 | 95.5 |
| | 50 + 100 | 90 | 73.0 | 80 | 70.0 | 65 | 60.0 | 100 | 98.9 |
| | 12.5 + 200 | 65 | 36.0 | 75 | 44.0 | 30 | 28.0 | 100 | 100.0 |
| | 25 + 200 | 70 | 44.0 | 80 | 52.0 | 50 | 46.0 | 100 | 100.0 |
| | 50 + 200 | 75 | 76.0 | 100 | 76.0 | 70 | 64.00 | 100 | 100.0 |

TABLE 8

| Component/species | | ECHCG (E) | | ECHCG (US) | | SAGPY | | SCPJU | | CYPDI | |
|---|---|---|---|---|---|---|---|---|---|---|---|
| A/B | Quantity (g/ha) | Activ. (%) | Colby (%) | Activ. (%) | Colby (%) | Activ. (%) | Colby (%) | Activ. (%) | Colby (%) | Activ. (%) | Colby (%) |
| A | 12.5 | 95 | | 45 | | 10 | | 10 | | 0 | |
|  | 25 | 98 | | 85 | | 25 | | 35 | | 10 | |
|  | 50 | 99 | | 100 | | 98 | | 60 | | 20 | |
| B8 | 25 | 90 | | 25 | | 55 | | 30 | | 20 | |
|  | 50 | 100 | | 70 | | 85 | | 40 | | 75 | |
|  | 10 | 100 | | 96 | | 98 | | 60 | | 80 | |
| A + B8 | 12.5 + 25 | 100 | 99.5 | 75 | 58.8 | 85 | 59.5 | 70 | 37.0 | 80 | 20.0 |
|  | 25 + 25 | 100 | 99.8 | 98 | 88.8 | 90 | 66.3 | 80 | 54.5 | 85 | 28.0 |
|  | 50 + 25 | 100 | 99.9 | 100 | 100 | 95 | 99.1 | 85 | 72.0 | 75 | 36.0 |
|  | 12.5 + 50 | 100 | 100 | 90 | 83.5 | 90 | 86.5 | 80 | 46.0 | 75 | 75.0 |
|  | 25 + 50 | 100 | 100 | 100 | 95.5 | 95 | 88.8 | 85 | 61.0 | 100 | 77.5 |
|  | 50 + 50 | 100 | 100 | 100 | 100 | 97 | 99.7 | 90 | 76.0 | 80 | 80.0 |
|  | 12.5 + 100 | 100 | 100 | 100 | 97.8 | 98 | 98.2 | 80 | 64.0 | 85 | 80.0 |
|  | 25 + 100 | 100 | 100 | 100 | 99.4 | 99 | 98.5 | 85 | 74.0 | 90 | 82.0 |
|  | 50 + 100 | 100 | 100 | 100 | 100 | 100 | 100 | 90 | 84.0 | 95 | 84.0 |

EXAMPLE 9

Mixtures of (A) with Trifluralin (B9)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5/25/50 g/ha and (B9) at rates of 250/500/1000 g/ha.

Synergistic effects were observed with ECHCG (E), CYPSE, SAGPY and CYPDI, as can be seen from Table 9 below.

TABLE 9

| Component/species | | ECHCG (E) | | CYPSE | | SAGPY | | CYPDI | |
|---|---|---|---|---|---|---|---|---|---|
| A/B | Quantity (g/ha) | Activ. (%) | Colby (%) | Activ. (%) | Colby (%) | Activ. (%) | Colby (%) | Activ. (%) | Colby (%) |
| A | 12.5 | 75 | | 30 | | 30 | | 0 | |
|  | 25 | 90 | | 45 | | 35 | | 20 | |
|  | 50 | 100 | | 80 | | 60 | | 30 | |
| B9 | 250 | 95 | | 0 | | 10 | | 60 | |
|  | 500 | 95 | | 0 | | 10 | | 75 | |
|  | 1000 | 100 | | 10 | | 20 | | 80 | |
| A + B9 | 12.5 + 250 | 95 | 98.8 | 30 | 30.0 | 30 | 37.0 | 75 | 60.0 |
|  | 25 + 250 | 100 | 95.5 | 40 | 45.0 | 35 | 41.5 | 85 | 68.0 |
|  | 50 + 250 | 100 | 100.0 | 80 | 80.0 | 70 | 64.0 | 90 | 72.0 |
|  | 12.5 + 500 | 100 | 98.8 | 30 | 30.0 | 30 | 37.0 | 80 | 75.0 |
|  | 25 + 500 | 100 | 99.5 | 60 | 45.0 | 40 | 41.5 | 85 | 80.0 |
|  | 50 + 500 | 100 | 100.0 | 80 | 80.0 | 75 | 64.0 | 90 | 82.5 |
|  | 12.5 + 1000 | 100 | 100.0 | 30 | 37.0 | 30 | 44.0 | 70 | 80.0 |
|  | 25 + 1000 | 100 | 100.0 | 70 | 50.5 | 50 | 48.0 | 85 | 84.0 |
|  | 50 + 1000 | 100 | 100.0 | 85 | 82.0 | 75 | 68.0 | 95 | 86.0 |

EXAMPLE 10

Mixtures of (A) with Bentazone (B10)

For the experiment, bentazone was applied at rates of 250/500/1000 g/ha and (A) at rates of 25/50/100 g/ha.

A synergistic effect was found in the mixing ratios 25 g/ha of (A)+250/500/1000 g/ha of bentazone, as can be seen from Table 10 below.

TABLE 10

| | | CYPDI | | |
|---|---|---|---|---|
| Dosage 1 (A) [g/ha] | Dosage 2 Bentazone g/ha | activity % | Calculated using Colby's formula % | Synergism |
| 25.0 | | 10.0 | | |
| 50.0 | | 100.0 | | |
| 100.0 | | 100.0 | | |

TABLE 10-continued

| | | CYPDI | | |
|---|---|---|---|---|
| Dosage 1 (A) [g/ha] | Dosage 2 Bentazone g/ha | activity % | Calculated using Colby's formula % | Synergism |
| | 250.0 | 0.0 | | |
| | 500.0 | 10.0 | | |
| | 1000.0 | 20.0 | | |

TABLE 10-continued

| | | CYPDI | | |
|---|---|---|---|---|
| Dosage 1 (A) [g/ha] | Dosage 2 Bentazone g/ha | activity % | Calculated using Colby's formula % | Synergism |
| 25.0 | 250.0 | 100.0 | 10.0 | + |
| 50.0 | 250.0 | 100.0 | 100.0 | |
| 100.0 | 250.0 | 100.0 | 100.0 | |
| 25.0 | 500.0 | 100.0 | 19.0 | + |
| 50.0 | 500.0 | 100.0 | 100.0 | |
| 100.0 | 500.0 | 100.0 | 100.0 | |
| 25.0 | 1000.0 | 100.0 | 28.0 | + |
| 50.0 | 1000.0 | 100.0 | 100.0 | |
| 100.0 | 1000.0 | 100.0 | 100.0 | |

EXAMPLE 11

Mixtures of (A) with Molinate (B11)

For the experiment, molinate was applied at rates of 250/500/1000 g/ha and (A) at rates of 25/50/100 g/ha.

With the mixing ratios used, a synergistic effect was found for European and American Echinochloa crus-galli and for the Cyperus species CYPSE and CYPDI, where the proportion of (A) was lower than the proportion of component (B11), as can be seen from Tables 11A and 11B below.

TABLE 11A

| | | ECHCG/European | | | ECHCG/American | | |
|---|---|---|---|---|---|---|---|
| Dosage 1 (A) g/ha | Dosage 2 g/ha Molinate | Activity % | Calculated using Colby's formula % | Synergism | Activity % | Calculated using Colby's formula % | Synergism |
| 25.0 | | 80.0 | | | 60.0 | | |
| 50.0 | | 99.0 | | | 100.0 | | |
| 100.0 | | 100.0 | | | 100.0 | | |
| | 250.0 | 10.0 | | | 20.0 | | |
| | 500.0 | 65.0 | | | 65.0 | | |
| | 1000.0 | 80.0 | | | 80.0 | | |
| 25.0 | 250.0 | 100.0 | 82.0 | + | 100.0 | 68.0 | + |
| 50.0 | 250.0 | 100.0 | 99.1 | + | 100.0 | 100.0 | |
| 100.0 | 250.0 | 100.0 | 100.0 | | 100.0 | 100.0 | |
| 25.0 | 500.0 | 100.0 | 93.0 | + | 100.0 | 86.0 | + |
| 50.0 | 500.0 | 100.0 | 99.7 | + | 100.0 | 100.0 | |
| 100.0 | 500.0 | 100.0 | 100.0 | | 100.0 | 100.0 | |
| 25.0 | 1000.0 | 100.0 | 96.0 | + | 100.0 | 92.0 | + |
| 50.0 | 1000.0 | 100.0 | 99.8 | + | 100.0 | 100.0 | |
| 100.0 | 1000.0 | 100.0 | 100.0 | | 100.0 | 100.0 | |

TABLE 11B

| | | CYPSE | | | CYPDI | | |
|---|---|---|---|---|---|---|---|
| Dosage 1 (A) g/ha | Dosage 2 g/ha Molinate | Activity % | Calculated using Colby's formula % | Synergism | Activity % | Calculated using Colby's formula % | Synergism |
| 25.0 | | | | | 50.0 | | |
| 50.0 | | 20.0 | | | 98.0 | | |
| 100.0 | | 100.0 | | | 100.0 | | |
| | 250.0 | 50.0 | | | 85.0 | | |
| | 500.0 | 60.0 | | | 90.0 | | |
| | 1000.0 | 70.0 | | | 92.0 | | |
| 25.0 | 250.0 | 95.0 | 50.0 | + | 85.0 | 92.5 | |
| 50.0 | 250.0 | 97.0 | 60.0 | + | 92.0 | 99.7 | |
| 100.0 | 250.0 | 98.0 | 100.0 | | 100.0 | 100.0 | |
| 25.0 | 500.0 | 30.0 | 60.0 | | 100.0 | 95.0 | + |
| 50.0 | 500.0 | 50.0 | 68.0 | | 100.0 | 99.8 | + |
| 100.0 | 500.0 | 100.0 | 100.0 | | 100.0 | 100.0 | |
| 25.0 | 1000.0 | 98.0 | 70.0 | + | 100.0 | 96.0 | + |
| 50.0 | 1000.0 | 100.0 | 76.0 | + | 100.0 | 99.8 | + |
| 100.0 | 1000.0 | 100.0 | 100.0 | | 100.0 | 100.0 | |

EXAMPLE 12

Mixtures of (A) with Daimuron (B12)

For the experiment, daimuron was applied at rates of 200/400/800 g/ha and (A) at rates of 25/50/100 g/ha.

For a variety of mixing ratios, a synergistic effect was observed with ECHCG (E), for the Cyperus species CYPSE and CYPDI and for SAGPY, as can be seen from Tables 12A, 12B and 12C below.

TABLE 12A

|  | | ECHCH (European) | | |
|---|---|---|---|---|
| Dosage 1 g/ha (A) | Dosage 2 g/ha Daimuron | Activity % | Calculated using Colby's formula % | Synergism |
| 25.0 |  | 75.0 |  |  |
| 50.0 |  | 98.0 |  |  |
| 100.0 |  | 100.0 |  |  |
|  | 200.0 | 25.0 |  |  |
|  | 400.0 | 25.0 |  |  |
|  | 800.0 | 65.0 |  |  |
| 25.0 | 200.0 | 70.0 | 81.3 |  |
| 50.0 | 200.0 | 99.0 | 98.5 | + |
| 100.0 | 200.0 | 100.0 | 100.0 |  |
| 25.0 | 400.0 | 90.0 | 81.3 | + |
| 50.0 | 400.0 | 100.0 | 98.5 | + |
| 100.0 | 400.0 | 100.0 | 100.0 |  |
| 25.0 | 800.0 | 80.0 | 91.3 |  |
| 50.0 | 800.0 | 100.0 | 99.3 | + |
| 100.0 | 800.0 | 100.0 | 100.0 |  |

TABLE 12B

|  | | CVPSE | | | CYPDI | | |
|---|---|---|---|---|---|---|---|
| Dosage 1 g/ha (A) | Dosage 2 g/ha Daimuron | Activity % | Calculated using Colby's formula % | Synergism | Activity % | Calculated using Colby's formula % | Synergism |
| 25.0 |  |  |  |  | 60.0 |  |  |
| 50.0 |  | 70.0 |  |  | 80.0 |  |  |
| 100.0 |  | 100.0 |  |  | 100.0 |  |  |
|  | 200.0 | 10.0 |  |  | 0.0 |  |  |
|  | 400.0 | 30.0 |  |  | 20.0 |  |  |
|  | 800.0 | 65.0 |  |  | 90.0 |  |  |
| 25.0 | 200.0 | 70.0 | 10.0 | + | 60.0 | 60.0 |  |
| 50.0 | 200.0 | 80.0 | 73.0 | + | 70.0 | 80.0 |  |
| 100.0 | 200.0 | 90.0 | 100.0 |  | 80.0 | 100.0 |  |
| 25.0 | 400.0 | 60.0 | 30.0 | + | 98.0 | 68.0 | + |
| 50.0 | 400.0 | 75.0 | 79.0 |  | 99.0 | 84.0 | + |
| 100.0 | 400.0 | 80.0 | 100.0 |  | 100.0 | 100.0 |  |
| 25.0 | 800.0 | 85.0 | 65.0 | + | 99.0 | 96.0 | + |
| 50.0 | 800.0 | 100.0 | 89.5 | + | 100.0 | 98.0 | + |
| 100.0 | 800.0 | 100.0 | 100.0 |  | 100.0 | 100.0 |  |

TABLE 12C

|  | | SAGPY | | |
|---|---|---|---|---|
| Dosage 1 g/ha (A) | Dosage 2 g/ha Daimuron | Activity % | Calculated using Colby's formula % | Synergism |
| 25.0 |  | 40.0 |  |  |
| 50.0 |  | 80.0 |  |  |
| 100.0 |  | 90.0 |  |  |
|  | 200.0 |  |  |  |
|  | 400.0 |  |  |  |
|  | 800.0 |  |  |  |
| 25.0 | 200.0 | 50.0 | 40.0 | + |
| 50.0 | 200.0 | 80.0 | 80.0 |  |
| 100.0 | 200.0 | 95.0 | 90.0 | + |
| 25.0 | 400.0 | 55.0 | 40.0 | + |
| 50.0 | 400.0 | 85.0 | 80.0 | + |
| 100.0 | 400.0 | 95.0 | 90.0 | + |
| 25.0 | 800.0 | 60.0 | 40.0 | + |
| 50.0 | 800.0 | 70.0 | 80.0 |  |
| 100.0 | 800.0 | 95.0 | 90.0 | + |

EXAMPLE 13

Mixtures of (A) with Thiobencarb (B13)

For the experiment, thiobencarb was applied at rates of 250/500/1000 g/ha and (A) at rates of 25/50/100 g/ha.

For some mixing ratios, a synergistic effect was observed with European Echinochloa crus-galli and for SAGPY, as shown in Table 13 below.

TABLE 13

| Dosage 1 g/ha (A) | Dosage 2 g/ha Thio-bencarb | ECHCG (European) | | | SAGPY | | |
|---|---|---|---|---|---|---|---|
| | | Activity % | Calculated using Colby's formula % | Synergism | Activity % | Calculated using Colby's formula % | Synergism |
| 25.0 | | 85.0 | | | 10.0 | | |
| 50.0 | | 98.0 | | | 85.0 | | |
| 100.0 | | 100.0 | | | 95.0 | | |
| | 250.0 | 65.0 | | | | | |
| | 500.0 | 90.0 | | | | | |
| | 1000.0 | 100.0 | | | | | |
| 25.0 | 250.0 | 98.0 | 94.8 | + | 50.0 | 10.0 | + |
| 50.0 | 250.0 | 99.0 | 99.3 | | 60.0 | 85.0 | |
| 100.0 | 250.0 | 100.0 | 100.0 | | 70.0 | 95.0 | |
| 25.0 | 500.0 | 98.0 | 98.5 | | 50.0 | 10.0 | + |
| 50.0 | 500.0 | 100.0 | 99.8 | + | 70.0 | 85.0 | |
| 100.0 | 500.0 | 100.0 | 100.0 | | 82.0 | 95.0 | |
| 25.0 | 1000.0 | 100.0 | 100.0 | | 55.0 | 10.0 | + |
| 50.0 | 1000.0 | 100.0 | 100.0 | | 75.0 | 85.0 | |
| 100.0 | 1000.0 | 100.0 | 100.0 | | 85.0 | 95.0 | |

EXAMPLE 14

Mixtures of (A) with Butachlor (B14)

For the experiment, butachlor was applied at rates of 250/500/1000 g/ha and (A) at rates of 25/50/100 g/ha.

For most mixing ratios, a synergistic effect was observed with SAGPY, as shown in Table 14 below.

TABLE 14

| Dosage 1 (A) g/ha | Dosage 2 Butachlor g/ha | SAGPY | | |
|---|---|---|---|---|
| | | Activity % | Calculated using Colby's formula % | Synergism |
| 25.0 | | 50.0 | | |
| 50.0 | | 70.0 | | |
| 100.0 | | 90.0 | | |
| | 250.0 | 20.0 | | |
| | 500.0 | 30.0 | | |
| | 1000.0 | 35.0 | | |
| 25.0 | 250.0 | 80.0 | 60.0 | + |
| 50.0 | 250.0 | 90.0 | 76.0 | + |
| 100.0 | 250.0 | 100.0 | 92.0 | + |

TABLE 14-continued

| Dosage 1 (A) g/ha | Dosage 2 Butachlor g/ha | SAGPY | | |
|---|---|---|---|---|
| | | Activity % | Calculated using Colby's formula % | Synergism |
| 25.0 | 500.0 | 40.0 | 65.0 | |
| 50.0 | 500.0 | 90.0 | 79.0 | + |
| 100.0 | 500.0 | 94.0 | 93.0 | + |
| 25.0 | 1000.0 | 60.0 | 67.5 | |
| 50.0 | 1000.0 | 90.0 | 80.5 | + |
| 100.0 | 1000.0 | 95.0 | 93.5 | + |

EXAMPLE 15

Mixtures of (A) with Pretilachlor (B15)

For the experiment, pretilachlor was employed at rates of 200/400/600 g/ha and (A) at rates of 25/50/100 g/ha.

For some mixing ratios, a synergistic effect was observed with SCPJU and CYPDI, as shown in Table 15 below.

TABLE 15

| Dosage 1 (A) g/ha | Dosage 2 Pretila-chlor g/ha | SCPJU | | | CYPDI | | |
|---|---|---|---|---|---|---|---|
| | | Activity % | Calculated using Colby's formula % | Synergism | Activity % | Calculated using Colby's formula % | Synergism |
| 25.0 | | 85.0 | | | 60.0 | | |
| 50.0 | | 90.0 | | | 80.0 | | |
| 100.0 | | 95.0 | | | 95.0 | | |
| | 200.0 | 80.0 | | | 90.0 | | |
| | 400.0 | 80.0 | | | 90.0 | | |
| | 600.0 | 80.0 | | | 95.0 | | |
| 25.0 | 200.0 | 98.0 | 97.0 | + | 95.0 | 96.0 | |
| 50.0 | 200.0 | 98.0 | 98.0 | | 100.0 | 98.0 | + |
| 100.0 | 200.0 | 99.0 | 99.0 | | 100.0 | 99.5 | + |
| 25.0 | 400.0 | 100.0 | 97.0 | + | 100.0 | 96.0 | + |
| 50.0 | 400.0 | 100.0 | 98.0 | + | 100.0 | 98.0 | + |
| 100.0 | 400.0 | 98.0 | 99.0 | | 98.0 | 99.5 | |

TABLE 15-continued

|  |  | SCPJU | | | CYPDI | | |
| --- | --- | --- | --- | --- | --- | --- | --- |
| Dosage 1 (A) g/ha | Dosage 2 Pretila-chlor g/ha | Activity % | Calculated using Colby's formula % | Synergism | Activity % | Calculated using Colby's formula % | Synergism |
| 25.0 | 600.0 | 98.0 | 97.0 | + | 95.0 | 98.0 | |
| 50.0 | 600.0 | 99.0 | 98.0 | + | 98.0 | 99.0 | |
| 100.0 | 600.0 | 98.0 | 99.0 | | 99.0 | 99.8 | |

EXAMPLE 16

Mixtures of (A) with Dimepiperate

For the experiment, dimepiperate was applied at rates of 250/500/1000 g/ha and (A) at rates of 25/50/100 g/ha.

For some mixing ratios, a synergistic effect was observed with SAGPY and CYPDI, as shown in Table 16 below.

TABLE 16

|  | Dosage 2 | CYPDI | | | SAGPY | | |
| --- | --- | --- | --- | --- | --- | --- | --- |
| Dosage 1 (A) g/ha | Dime-piper-ate g/ha | Activity % | Calculated using Colby's formula % | Synergism | Activity % | Calculated using Colby's formula % | Synergism |
| 25.0 |  | 70.0 | | | 0.0 | | |
| 50.0 |  | 80.0 | | | 50.0 | | |
| 100.0 |  | 90.0 | | | 80.0 | | |
|  | 250.0 | 0.0 | | | | | |
|  | 500.0 | 30.0 | | | | | |
|  | 1000.0 | 60.0 | | | | | |
| 25.0 | 250.0 | 100.0 | 70.0 | + | 20.0 | 0.0 | + |
| 50.0 | 250.0 | 100.0 | 80.0 | + | 50.0 | 50.0 | |
| 100.0 | 250.0 | 100.0 | 90.0 | + | 75.0 | 80.0 | |
| 25.0 | 500.0 | 100.0 | 79.0 | + | 20.0 | 0.0 | + |
| 50.0 | 500.0 | 100.0 | 86.0 | + | 50.0 | 50.0 | |
| 100.0 | 500.0 | 100.0 | 93.0 | + | 75.0 | 80.0 | |
| 25.0 | 1000.0 | 100.0 | 88.0 | + | 25.0 | 0.0 | + |
| 50.0 | 1000.0 | 100.0 | 92.0 | + | 70.0 | 50.0 | + |
| 100.0 | 1000.0 | 100.0 | 96.0 | + | 90.0 | 80.0 | + |

EXAMPLE 17

Mixtures of (A) with Fenoxaprop-ethyl (B17)

For the experiment, fenoxaprop-ethyl was applied at rates of 5/10/20 g/ha and (A) at rates of 25/50/100 g/ha.

For some mixing ratios, a synergistic effect was observed with ECHCG(USA) and CYPDI, as shown in Table 17 below.

TABLE 17

|  |  | ECHCG (American) | | | CYPDI | | |
| --- | --- | --- | --- | --- | --- | --- | --- |
| Dosage 1 (A) g/ha | Dosage 2 Fenoxa-propethyl g/ha | Activity % | Calculated using Colby's formula % | Synergism | Activity % | Calculated using Colby's formula % | Synergism |
| 25.0 |  | 98.0 | | | 90.0 | | |
| 50.0 |  | 99.0 | | | 90.0 | | |
| 100.0 |  | 100.0 | | | 95.0 | | |
|  | 5.0 | 10.0 | | | 0.0 | | |

TABLE 17-continued

|  | | ECHCG (American) | | | CYPDI | | |
|---|---|---|---|---|---|---|---|
| Dosage 1 (A) g/ha | Dosage 2 Fenoxa-propethyl g/ha | Activity % | Calculated using Colby's formula % | Synergism | Activity % | Calculated using Colby's formula % | Synergism |
|  | 10.0 | 20.0 |  |  | 0.0 |  |  |
|  | 20.0 | 0.0 |  |  | 80.0 |  |  |
| 25.0 | 5.0 | 25.0 | 98.2 |  | 80.0 | 90.0 |  |
| 50.0 | 5.0 | 100.0 | 99.1 | + | 90.0 | 92.0 |  |
| 100.0 | 5.0 | 100.0 | 100.0 |  | 100.0 | 95.0 | + |
| 25.0 | 10.0 | 25.0 | 98.4 |  | 95.0 | 90.0 | + |
| 50.0 | 10.0 | 98.0 | 99.2 |  | 100.0 | 92.0 | + |
| 100.0 | 10.0 | 100.0 | 100.0 |  | 100.0 | 95.0 | + |
| 25.0 | 20.0 | 10.0 | 98.0 |  | 40.0 | 98.0 |  |
| 50.0 | 20.0 | 100.0 | 99.0 | + | 100.0 | 98.4 | + |
| 100.0 | 20.0 | 100.0 | 100.0 |  | 100.0 | 99.0 | + |

EXAMPLE 18

Mixtures of (A) with Clomeprop (B18)

For the experiment, clomeprop was applied at rates of 200/400/800 g/ha and (A) at rates of 25/50/100 g/ha.

For some mixing ratios, a synergistic effect was observed with CYPDI, as shown in Table 18 below.

TABLE 18

|  | | CYPDI | | |
|---|---|---|---|---|
| Dosage 1 (A) g/ha | Dosage 2 Clome-prop g/ha | Activity % | Calculated using Colby's formula % | Synergism |
| 25.0 |  | 70.0 |  |  |
| 50.0 |  | 75.0 |  |  |
| 100.0 |  | 90.0 |  |  |
| 25.0 | 200.0 | 95.0 |  |  |
| 50.0 | 400.0 | 100.0 |  |  |
| 100.0 | 800.0 | 100.0 |  |  |
| 25.0 | 200.0 | 100.0 | 98.5 | + |
| 50.0 | 200.0 | 100.0 | 98.8 | + |
| 100.0 | 200.0 | 100.0 | 99.5 | + |

TABLE 18-continued

|  | | CYPDI | | |
|---|---|---|---|---|
| Dosage 1 (A) g/ha | Dosage 2 Clome-prop g/ha | Activity % | Calculated using Colby's formula % | Synergism |
| 25.0 | 400.0 | 100.0 | 100.0 |  |
| 50.0 | 400.0 | 100.0 | 100.0 |  |
| 100.0 | 400.0 | 100.0 | 100.0 |  |
| 25.0 | 800.0 | 100.0 | 100.0 |  |
| 50.0 | 800.0 | 100.0 | 100.0 |  |
| 100.0 | 800.0 | 100.0 | 100.0 |  |

EXAMPLE 19

Mixtures of (A) with Cinmethylin (B19)

For the experiment, cinmethylin was applied at rates of 10/20/40 g/ha and (A) at rates of 25/50/100 g/ha.

For some mixing ratios, a synergistic effect was observed with ECHCG(European) and CYPDI, as shown in Table 19 below.

TABLE 19

|  | | ECHCG (European) | | | CYPDI | | |
|---|---|---|---|---|---|---|---|
| Dosage 1 (A) g/ha | Dosage 2 methylin g/ha | Activity % | Calculated using Colby's formula % | Synergism | Activity % | Calculated using Colby's formula % | Synergism |
| 25.0 |  | 95.0 |  |  | 30.0 |  |  |
| 50.0 |  | 99.0 |  |  | 80.0 |  |  |
| 100.0 |  | 100.0 |  |  | 90.0 |  |  |
|  | 10.0 | 60.0 |  |  | 60.0 |  |  |
|  | 20.0 | 100.0 |  |  | 60.0 |  |  |
|  | 40.0 | 100.0 |  |  | 60.0 |  |  |
| 25.0 | 10.0 | 99.0 | 98.0 | + | 30.0 | 72.0 |  |
| 50.0 | 10.0 | 100.0 | 99.6 | + | 98.0 | 92.0 | + |
| 100.0 | 10.0 | 100.0 | 100.0 |  | 98.0 | 96.0 | + |
| 25.0 | 20.0 | 100.0 | 100.0 |  | 90.0 | 72.0 | + |
| 50.0 | 20.0 | 100.0 | 100.0 |  | 100.0 | 92.0 | + |
| 100.0 | 20.0 | 100.0 | 100.0 |  | 100.0 | 96.0 | + |

TABLE 19-continued

| Dosage 1 (A) g/ha | Dosage 2 methylin g/ha | ECHCG (European) | | | CYPDI | | |
|---|---|---|---|---|---|---|---|
| | | Activity % | Calculated using Colby's formula % | Synergism | Activity % | Calculated using Colby's formula % | Synergism |
| 25.0 | 40.0 | 100.0 | 100.0 | | 100.0 | 72.0 | + |
| 50.0 | 40.0 | 100.0 | 100.0 | | 100.0 | 92.4 | + |
| 100.0 | 40.0 | 100.0 | 100.0 | | 100.0 | 96.0 | + |

EXAMPLE 20

Mixtures of (A) with Bromobutide (B20)

For the experiment, bromobutide was applied at rates of 100/200/400 g/ha and (A) at rates of 25/50/100 g/ha.

For some mixing ratios, a synergistic effect was observed with ECHCG(European) and ECHCG (American), as shown in Table 20 below.

TABLE 20

| Dosage 1 (A) g/ha | Dosage 2 Bromo-butide g/ha | ECHCG (European) | | | ECHCG (American) | | |
|---|---|---|---|---|---|---|---|
| | | Activity % | Calculated using Colby's formula % | Synergism | Activity % | Calculated using Colby's formula % | Synergism |
| 25.0 | | 50.0 | | | 65.0 | | |
| 50.0 | | 98.0 | | | 99.0 | | |
| 100.0 | | 100.0 | | | 100.0 | | |
| | 200.0 | 10.0 | | | 5.0 | | |
| | 400.0 | 25.0 | | | 10.0 | | |
| | 800.0 | 30.0 | | | 40.0 | | |
| 25.0 | 200.0 | 90.0 | 55.0 | + | 80.0 | 66.8 | + |
| 50.0 | 200.0 | 100.0 | 98.2 | + | 100.0 | 99.1 | + |
| 100.0 | 200.0 | 100.0 | 100.0 | | 100.0 | 100.0 | |
| 25.0 | 400.0 | 95.0 | 62.5 | + | 98.0 | 68.5 | + |
| 50.0 | 400.0 | 100.0 | 98.5 | + | 100.0 | 99.1 | + |
| 100.0 | 400.0 | 100.0 | 100.0 | | 100.0 | 100.0 | |
| 25.0 | 800.0 | 100.0 | 65.0 | + | 100.0 | 79.0 | + |
| 50.0 | 800.0 | 100.0 | 98.6 | + | 100.0 | 99.4 | + |
| 100.0 | 800.0 | 100.0 | 100.0 | | 100.0 | 100.0 | |

EXAMPLE 21

Mixtures of (A) with Quinclorac (B21)

For the experiment, Quinclorac was applied at rates of 250/500/1000 g/ha and (A) at rates of 25/50/100 g/ha.

For some mixing ratios, a synergistic effect was observed with CYPSE and SCPJU, as shown in Table 21 below.

TABLE 21

| Dosage 1 A0 g/ha | Dosage 2 Quinclorac g/ha | CYPSE Activity | Calculated using Colby's formula % | Syner-gism | SCPJU Activity | Calculated using Colby's formula % | Syner-gism |
|---|---|---|---|---|---|---|---|
| 25.0 | | 0.0 | | | 98.0 | | |
| 50.0 | | 10.0 | | | 100.0 | | |
| 100.0 | | 95.0 | | | 100.0 | | |
| | 250.0 | 0.0 | | | 0.0 | | |

TABLE 21-continued

| Dosage 1 A0 g/ha | Dosage 2 Quinclorac g/ha | CYPSE Activity | Calculated using Colby's formula % | Synergism | SCPJU Activity | Calculated using Colby's formula % | Synergism |
|---|---|---|---|---|---|---|---|
| | 500.0 | 0.0 | | | 10.0 | | |
| | 1000.0 | 0.0 | | | 50.0 | | |
| 25.0 | 250.0 | 0.0 | | | 99.0 | 98.0 | + |
| 50.0 | 250.0 | 50.0 | 10.0 | + | 100.0 | 100.0 | |
| 100.0 | 250.0 | 95.0 | 95.0 | | 100.0 | 100.0 | |
| 25.0 | 500.0 | 0.0 | 0.0 | | 100.0 | 98.2 | + |
| 50.0 | 500.0 | 50.0 | 10.0 | + | 100.0 | 100.0 | |
| 100.0 | 500.0 | 100.0 | 95.0 | + | 100.0 | 100.0 | |
| 25.0 | 1000.0 | 10.0 | 0.0 | + | 100.0 | 99.0 | + |
| 50.0 | 1000.0 | 50.0 | 10.0 | + | 100.0 | 100.0 | |
| 100.0 | 1000.0 | 100.0 | 95.0 | + | 100.0 | 100.0 | |

EXAMPLE 22

Mixtures of (A) with Mefenacet (B22)

For the experiment, mefenacet was applied at rates of 250/500/1000 g/ha and (A) at rates of 25/50/100 g/ha.

For some mixing ratios, a synergistic effect was observed with SAGPY, as shown in Table 21 below.

TABLE 22

| Dosage 1 (A) g/ha | Dosage 2 Mefenacet g/ha | SAGPY Activity % | Calculated using Colby's formula % | Synergism |
|---|---|---|---|---|
| 25.0 | | | | |
| 50.0 | | 30.0 | | |
| 100.0 | | 40.0 | | |
| | 250.0 | 0.0 | | |
| | 500.0 | 20.0 | | |
| | 1000.0 | 40.0 | | |
| 25.0 | 250.0 | 30.0 | 0.0 | + |
| 50.0 | 250.0 | 50.0 | 30.0 | + |
| 100.0 | 250.0 | 80.0 | 40.0 | + |
| 25.0 | 500.0 | 30.0 | 20.0 | + |
| 50.0 | 500.0 | 50.0 | 44.0 | + |
| 100.0 | 500.0 | 80.0 | 52.0 | + |
| 25.0 | 1000.0 | 30.0 | 40.0 | |
| 50.0 | 1000.0 | 75.0 | 58.0 | + |
| 100.0 | 1000.0 | 90.0 | 64.0 | + |

EXAMPLE 23

Mixtures of (A) with Pyrazosulforon-ethyl (B23)

For the experiment, pyrazosulforon-ethyl was applied at rates of 10/40 g/ha and (A) at rates of 25/50/100 g/ha.

For some mixing ratios, a synergistic effect was observed with CYPDI, as shown in Table 23 below.

TABLE 23

| Dosage 1 g/ha (A) | Dosage 2 g/ha Pyrazosulfuron-ethyl | CYPDI Activity % | Calculated using Colby's formula % | Synergism |
|---|---|---|---|---|
| 25.0 | | 90.0 | | |
| 50.0 | | 90.0 | | |
| 100.0 | | 70.0 | | |
| | 10.0 | 95.0 | | |
| | 40.0 | 70.0 | | |
| 25.0 | 10.0 | 95.0 | 99.5 | |
| 50.0 | 10.0 | 90.0 | 99.5 | |
| 100.0 | 10.0 | 100.0 | 98.5 | + |
| 25.0 | 40.0 | 75.0 | 97.0 | |
| 50.0 | 40.0 | 100.0 | 97.0 | + |
| 100.0 | 40.0 | 100.0 | 91.0 | + |

EXAMPLE 24

Mixtures of (A) with Esprocarb (B24)

For the experiment, esprocarb was applied at rates of 200/400/800 g/ha and (A) at rates of 25/50/100 g/ha.

For some mixing ratios, a synergistic effect was observed with ECHCG (European) and SCPJU, as shown in Table 24 below.

TABLE 24

| Dosage 1 (A) g/ha | Dosage 2 Esprocarb g/ha | ECHCH (European) Activity | Calculated using Colby's formula % | Synergism | SCPJU Activity | Calculated using Colby's formula % | Synergism |
|---|---|---|---|---|---|---|---|
| 25.0 | | 95.0 | | | 95.0 | | |
| 50.0 | | 99.0 | | | 97.0 | | |
| 100.0 | | 100.0 | | | 99.0 | | |
| | 200.0 | 20.0 | | | 45.0 | | |

TABLE 24-continued

| Dosage 1 (A) g/ha | Dosage 2 Esprocarb g/ha | ECHCH (European) Activity | Calculated using Colby's formula % | Synergism | SCPJU Activity | Calculated using Colby's formula % | Synergism |
|---|---|---|---|---|---|---|---|
|  | 400.0 | 80.0 |  |  | 80.0 |  |  |
|  | 800.0 | 80.0 |  |  | 85.0 |  |  |
| 25.0 | 200.0 | 99.0 | 96.0 | + | 100.0 | 97.3 | + |
| 50.0 | 200.0 | 100.0 | 99.2 | + | 100.0 | 98.4 | + |
| 100.0 | 200.0 | 100.0 | 100.0 |  | 100.0 | 99.5 | + |
| 25.0 | 400.0 | 92.0 | 99.0 |  | 99.0 | 99.0 |  |
| 50.0 | 400.0 | 100.0 | 99.8 | + | 99.0 | 99.4 |  |
| 100.0 | 400.0 | 100.0 | 100.0 |  | 100.0 | 99.8 | + |
| 25.0 | 800.0 | 99.0 | 99.0 |  | 99.0 | 99.3 |  |
| 50.0 | 800.0 | 100.0 | 99.8 | + | 99.0 | 99.6 |  |
| 100.0 | 800.0 | 100.0 | 100.0 |  | 100.0 | 99.9 | + |

EXAMPLE 25

Mixtures of (A) with Cinosulfuron (B25)

For the experiment, cinosulfuron was applied at rates of 25/75 g/ha and (A) at rates of 25/50/100 g/ha.

For some mixing ratios, a synergistic effect was observed with CYPSE, as shown in Table 25 below.

TABLE 25

| Dosage 1 (A) g/ha | Dosage 2 Cinosulfuron g/ha | CYPSE Activity % | Calculated using Colby's formula % | Synergism |
|---|---|---|---|---|
| 25.0 |  | 0.0 |  |  |
| 50.0 |  | 10.0 |  |  |
| 100.0 |  | 20.0 |  |  |
|  | 25.0 | 0.0 |  |  |
|  | 75.0 | 45.0 |  |  |
| 25.0 | 25.0 | 0.0 | 0.0 |  |
| 50.0 | 25.0 | 20.0 | 10.0 | + |
| 100.0 | 25.0 | 20.0 | 20.0 |  |
| 25.0 | 75.0 | 60.0 | 45.0 | + |
| 50.0 | 75.0 | 70.0 | 50.5 | + |
| 100.0 | 75.0 | 85.0 | 56.0 | + |

EXAMPLE 26

Mixtures of (A) with Thenylchlor (B26)

For the experiment, thenylchlor was applied at rates of 25/50/75 g/ha and (A) at rates of 25/50/100 g/ha.

For some mixing ratios, a synergistic effect was observed with ECHCG (European), CYPSE and SAGPY, as shown in Tables 26A and 26B below.

TABLE 26A

| Dosage 1 (A) g/ha | Dosage 2 Thenylchlor g/ha | ECHCG (European) Activity % | Calculated using Colby's formula % | Synergism |
|---|---|---|---|---|
| 25.0 |  | 55.0 |  |  |
| 50.0 |  | 97.0 |  |  |
| 100.0 |  | 99.0 |  |  |
|  | 25.0 | 10.0 |  |  |
|  | 50.0 | 96.0 |  |  |
|  | 75.0 | 98.0 |  |  |
| 25.0 | 25.0 | 80.0 | 59.5 | + |
| 50.0 | 25.0 | 98.0 | 97.3 | + |
| 100.0 | 25.0 | 99.0 | 99.1 |  |
| 25.0 | 50.0 | 100.0 | 98.2 | + |
| 50.0 | 50.0 | 100.0 | 99.9 | + |
| 100.0 | 50.0 | 100.0 | 100.0 | + |
| 25.0 | 75.0 | 100.0 | 99.1 | + |
| 50.0 | 75.0 | 100.0 | 99.9 | + |
| 100.0 | 75.0 | 100.0 | 100.0 | + |

TABLE 26B

| Dosage 1 (A) g/ha | Dosage 2 Thenylchlor g/ha | CYPSE Activity % | Calculated using Colby's formula % | Synergism | SAGPY Activity | Calculated using Colby's formula | Synergism |
|---|---|---|---|---|---|---|---|
| 25.0 |  | 0.0 |  |  | 55.0 |  |  |
| 50.0 |  | 10.0 |  |  | 70.0 |  |  |
| 100.0 |  | 95.0 |  |  | 85.0 |  |  |
|  | 25.0 | 10.0 |  |  | 0.0 |  |  |
|  | 50.0 | 30.0 |  |  | 0.0 |  |  |
|  | 75.0 | 80.0 |  |  | 10.0 |  |  |
| 25.0 | 25.0 | 0.0 | 10.0 |  | 50.0 | 55.0 |  |
| 50.0 | 25.0 | 90.0 | 19.0 | + | 70.0 | 70.0 |  |
| 100.0 | 25.0 | 95.0 | 95.5 |  | 90.0 | 85.0 | + |
| 25.0 | 50.0 | 0.0 | 30.0 |  | 70.0 | 55.0 | + |

TABLE 26B-continued

| Dosage 1 (A) g/ha | Dosage 2 Thenylchlor g/ha | CYPSE Activity % | Calculated using Colby's formula % | Synergism | SAGPY Activity | Calculated using Colby's formula | Synergism |
|---|---|---|---|---|---|---|---|
| 50.0 | 50.0 | 0.0 | 37.0 |   | 80.0 | 70.0 | + |
| 100.0 | 50.0 | 0.0 | 96.5 |   | 90.0 | 85.0 | + |
| 25.0 | 75.0 | 95.0 | 80.0 | + | 30.0 | 59.5 |   |
| 50.0 | 75.0 | 97.0 | 82.0 | + | 90.0 | 73.0 | + |
| 100.0 | 75.0 | 98.0 | 99.0 |   | 90.0 | 86.5 | + |

EXAMPLE 27

Mixtures of (A) with Cumyluron (B27)

For the experiment, cumyluron was applied at rates of 25/50/75 g/ha and (A) at rates of 25/50/100 g/ha.

For some mixing ratios, a synergistic effect was observed with ECHCG (European) and ECHCG (American), as shown in Table 27 below

TABLE 27

| Dosage 1 (A) g/ha | Dosage 2 Cumyluron g/ha | ECHCG (Europoean) Activity | Calculated using Colby's formula % | Synergism | ECHCG (American) Activity | Calculated using Colby's formula % | Synergism |
|---|---|---|---|---|---|---|---|
| 25.0 |   | 90.0 |   |   | 93.0 |   |   |
| 50.0 |   | 100.0 |   |   | 100.0 |   |   |
| 100.0 |   | 100.0 |   |   | 100.0 |   |   |
|   | 25.0 | 0.0 |   |   | 0.0 |   |   |
|   | 50.0 | 20.0 |   |   | 10.0 |   |   |
|   | 75.0 | 30.0 |   |   | 20.0 |   |   |
| 25.0 | 25.0 | 95.0 | 90.0 | + | 95.0 | 93.0 | + |
| 50.0 | 25.0 | 100.0 | 100.0 |   | 100.0 | 100.0 |   |
| 100.0 | 25.0 | 100.0 | 100.0 |   | 100.0 | 100.0 |   |
| 25.0 | 50.0 | 95.0 | 92.0 | + | 95.0 | 93.7 | + |
| 50.0 | 50.0 | 100.0 | 100.0 |   | 100.0 | 100.0 |   |
| 100.0 | 50.0 | 100.0 | 100.0 |   | 100.0 | 100.0 |   |
| 25.0 | 75.0 | 70.0 | 93.0 |   | 95.0 | 94.4 | + |
| 50.0 | 75.0 | 100.0 | 100.0 |   | 100.0 | 100.0 |   |
| 100.0 | 75.0 | 100.0 | 100.0 |   | 100.0 | 100.0 |   |

EXAMPLE 28

Mixtures if (A) with MK 243 (B28)

For the experiment, MK 243 was applied at rates of 25/50/75 g/ha and (A) at rates of 25/50/100 g/ha, MK 243 was present as a WP20 formulation, and (A) as a WP5 formulation.

For some mixing ratios, a synergistic effect was found with CYPSE and CYDPI, as can be seen in Table 28 below.

TABLE 28

| Dosage 1 (A) g/ha | Dosage 2 MK 243 g/ha | CYPSE Activity | Calculated using Colby's formula % | Synergism | CYPDI Activity | Calculated using Colby's formula % | Syngergism |
|---|---|---|---|---|---|---|---|
| 25.0 |   | 0.0 |   |   | 98.0 |   |   |
| 50.0 |   | 40.0 |   |   | 99.0 |   |   |
| 100.0 |   | 100.0 |   |   | 100.0 |   |   |
|   | 25.0 | 0.0 |   |   | 0.0 |   |   |
|   | 50.0 | 0.0 |   |   | 0.0 |   |   |
|   | 75.0 | 10.0 |   |   | 30.0 |   |   |
| 25.0 | 25.0 | 0.0 | 0.0 |   | 100.0 | 98.0 | + |

TABLE 28-continued

| Dosage 1 (A) g/ha | Dosage 2 MK 243 g/ha | CYPSE Activity | Calculated using Colby's formula % | Synergism | CYPDI Activity | Calculated using Colby's formula % | Syngergism |
|---|---|---|---|---|---|---|---|
| 50.0 | 25.0 | 40.0 | 40.0 | | 100.0 | 99.0 | + |
| 100.0 | 25.0 | 90.0 | 100.0 | | 100.0 | 100.0 | |
| 25.0 | 50.0 | 30.0 | 0.0 | + | 95.0 | 98.0 | |
| 50.0 | 50.0 | 50.0 | 40.0 | + | 98.0 | 99.0 | |
| 100.0 | 50.0 | 96.0 | 100.0 | | 100.0 | 100.0 | |
| 25.0 | 75.0 | 100.0 | 10.0 | + | 100.0 | 98.6 | + |
| 50.0 | 75.0 | 100.0 | 46.0 | + | 100.0 | 99.3 | + |

EXAMPLE 29

Mixtures of (A) with Naproanilide (B29)

For the experiment, naproanilide was applied at rates of 500/625/750 g/ha and (A) at rates of 100/125/150 g/ha.

For some mixing ratios, a synergistic effect was observed with CYPSE, as shown in Table 29 below.

TABLE 29

| Dosage 1 (A) g/ha | Dosage 2 Naproanilide g/ha | CYPSE Activity | Calculated using Colby's formula | Synergism |
|---|---|---|---|---|
| 100.0 | | 95.0 | | |
| 125.0 | | 85.0 | | |
| 150.0 | | 80.0 | | |
| | 500.0 | 0.0 | | |
| | 625.0 | 0.0 | | |
| | 750.0 | 0.0 | | |
| 100.0 | 500.0 | 88.0 | 95.0 | |
| 125.0 | 500.0 | 90.0 | 85.0 | + |
| 150.0 | 500.0 | 85.0 | 80.0 | + |
| 100.0 | 625.0 | 90.0 | 95.0 | |
| 125.0 | 625.0 | 90.0 | 85.0 | + |
| 150.0 | 625.0 | 70.0 | 80.0 | |
| 100.0 | 750.0 | 90.0 | 95.0 | |
| 125.0 | 750.0 | 95.0 | 85.0 | + |
| 150.0 | 750.0 | 70.0 | 80.0 | |

EXAMPLE 30

Mixtures of (A) with Anilofos (B30)

For the experiment, anilofos was applied at rates of 62.5/93.8/125 g/ha and (A) at rates of 50/75/100 g/ha.

For all mixing ratios tested, a synergistic effect was found with CYPSE, as can be seen in Table 30 below.

TABLE 30

| Dosage 1 (A) g/ha | Dosage 2 Anilofos g/ha | CYPSE Activity | Calculated using Colby's formula % | Synergism |
|---|---|---|---|---|
| 50.0 | | 80.0 | | |
| 75.0 | | 80.0 | | |
| 100.0 | | 80.0 | | |
| | 62.5 | 0.0 | | |
| | 93.8 | 0.0 | | |
| | 125.0 | 0.0 | | |
| 50.0 | 62.5 | 90.0 | 80.0 | + |
| 75.0 | 62.5 | 95.0 | 80.0 | + |
| 100.0 | 62.5 | 95.0 | 80.0 | + |
| 50.0 | 93.8 | 90.0 | 80.0 | + |
| 75.0 | 93.8 | 85.0 | 80.0 | + |
| 100.0 | 93.8 | 95.0 | 80.0 | + |
| 50.0 | 125.0 | 90.0 | 80.0 | + |
| 75.0 | 125.0 | 85.0 | 80.0 | + |
| 100.0 | 125.0 | 90.0 | 80.0 | + |

EXAMPLE 31

Mixtures of (A) with Benfuresate (B31)

For the experiment, benfuresate was applied at rates of 150/200/250 g/ha and (A) at rates of 50/75/100 g/ha.

For some mixing ratios, a synergistic effect was observed with CYPDI, as shown in Table 31 below.

TABLE 31

| Dosage 1 (A) g/ha | Dosage 2 Benfuresate g/ha | CYPDI Activity % | Calculated using Colby's formula % | Synergism |
|---|---|---|---|---|
| 50.0 | | 90.0 | | |
| 75.0 | | 100.0 | | |
| 100.0 | | 100.0 | | |
| | 150.0 | 0.0 | | |
| | 200.0 | 0.0 | | |
| | 250.0 | 60.0 | | |
| 50.0 | 150.0 | 100.0 | 90.0 | + |
| 75.0 | 150.0 | 100.0 | 100.0 | |
| 100.0 | 150.0 | 100.0 | 100.0 | |
| 50.0 | 200.0 | 100.0 | 90.0 | + |
| 75.0 | 200.0 | 100.0 | 100.0 | |
| 100.0 | 200.0 | 100.0 | 100.0 | |
| 50.0 | 250.0 | 100.0 | 96.0 | + |
| 75.0 | 250.0 | 100.0 | 100.0 | |
| 100.0 | 250.0 | 100.0 | 100.0 | |

EXAMPLE 32

Mixtures of (A) with Piperophos (B32)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 25 and 100 g/ha and piperophos at rates of 400 and 800 g/ha.

For some mixing ratios, a synergistic effect was observed with SCPJU, as shown in Table 32 below.

TABLE 32

| Dosage 1 (A) | Dosage 2 Piperophos | SCPJU activity (%) | Calculated using Colby's formula | Synergism |
|---|---|---|---|---|
| 25 | | 65 | | |
| 100 | | 95 | | |
| | 400 | 92 | | |
| | 800 | 94 | | |
| 25 | 800 | 99 | 98 | + |
| 100 | 800 | 100 | 99.7 | + |

EXAMPLE 33

Mixtures of (A) with Pyributicarb (B33)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 25 and 50 g/ha and pyributicarb at rates of 200 and 400 g/ha.

For some mixing ratios, a synergistic effect was observed with ECHCG, as shown in Table 33 below.

TABLE 33

| Dosage 1 (A) | Dosage 2 Pyributi-carb | ECHCG activity (%) | Calculated using Colby's formula | Synergism |
|---|---|---|---|---|
| 25 | | 87 | | |
| 50 | | 99 | | |
| | 200 | 80 | | |
| | 400 | 99 | | |
| 25 | 200 | 98 | 97.4 | + |
| 25 | 400 | 100 | 99.9 | + |

EXAMPLE 34

Mixtures of (A) with Ethoxysulfuron (B34)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 12.5 D 25 I 50 g/ha and ethoxysulfuron at rates of 5, 10 and 20 g/ha.

For some mixing ratios, a synergistic effect was observed with ECHCG (2,5-leaf stage), as shown in Table 34 below.

TABLE 34

| Dosage 1 (A) | Dosage 2 Eghoxysul-foron | ECHCG activity (%) | Calculated using Colby's formula | Synergism |
|---|---|---|---|---|
| 12.5 | | 30 | | |
| 25 | | 50 | | |
| 50 | | 75 | | |
| | 5 | 0 | | |
| | 10 | 10 | | |
| | 20 | 20 | | |
| 12.5 | 5 | 30 | 30 | − |
| 25 | 5 | 60 | 50 | + |
| 50 | 5 | 98 | 75 | + |
| 12.5 | 10 | 45 | 37 | + |
| 25 | 10 | 65 | 55 | + |
| 50 | 10 | 98 | 77.5 | + |
| 12.5 | 20 | 45 | 44 | + |

TABLE 34-continued

| Dosage 1 (A) | Dosage 2 Eghoxysul-foron | ECHCG activity (%) | Calculated using Colby's formula | Synergism |
|---|---|---|---|---|
| 25 | 20 | 65 | 60 | + |
| 50 | 20 | 98 | 80 | + |

EXAMPLE 35

Mixtures of (A) with Bensulfuron-methyl (B35)

For the experiment, 1-(3-chloro-4,5,6,7,-tetrahydropyrazolo-[1,5-a]-pyridin-2-yl)-5-(methylpropargylamino)-4-pyrazolylcarbonitrile (A) was applied at rates of 12.5 and 25 g/ha and bensulfuronmethyl at rates of 10 and 20 g/ha.

A synergistic effect was observed with ECHCG (2,5-leaf stage), as shown in Table 35 below.

TABLE 35

| Dosage 1 (A) | Dosage 2 Bensulfur-on-methyl | ECHCG activity (%) | Calculated using Colby's formula | Synergism |
|---|---|---|---|---|
| 12.5 | | 20 | | |
| 25 | | 40 | | |
| | 10 | 40 | | |
| | 20 | 70 | | |
| 25 | 10 | 70 | 64 | + |

EXAMPLE 36

Mixtures of (A) with Pyrazolate (B36)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 50 and 100 g/ha and pyrazolate at rates of 500 and 1000 g/ha.

For some mixing ratios, a synergistic effect was observed with PASDS, as shown in Table 36 below.

TABLE 36

| Dosage 1 (A) | Dosage 2 Pyrazolate | PASDS activity (%) | Calculated using Colby's formula | Synergism |
|---|---|---|---|---|
| 50 | | 70 | | |
| 100 | | 80 | | |
| | 500 | 0 | | |
| | 1000 | 0 | | |
| 50 | 500 | 70 | 70 | − |
| 100 | 500 | 95 | 80 | + |
| 100 | 1000 | 100 | 80 | + |

EXAMPLE 37

Mixtures of (A) with Pyrazoxyfen (B37)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 50 and 100 g/ha and pyrazoxyfen at rates of 500 and 1000 g/ha.

For some mixing ratios, a synergistic effect was observed with PASDS, as shown in Table 37 below.

TABLE 37

| Dosage 1 (A) | Dosage 2 Pyrazoxyfen | PASDS activity (%) | Calculated using Colby's formula | Synergism |
|---|---|---|---|---|
| 50 |  | 10 |  |  |
| 100 |  | 98 |  |  |
|  | 500 | 0 |  |  |
|  | 1000 | 0 |  |  |
| 50 | 500 | 20 | 10 | + |
| 100 | 500 | 98 | 98 | − |
| 50 | 1000 | 30 | 10 | + |

EXAMPLE 38

Mixtures of (A) with Benzofenap (B38)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at a rate of 50 g/ha and benzofenap at rates of 500 and 1000 g/ha.

A synergistic effect was observed with ECHCG, as shown in Table 38 below.

TABLE 38

| Dosage 1 (A) | Dosage 2 Benzofenap | ECHCG activity (%) | Calculated using Colby's formula | Synergism |
|---|---|---|---|---|
| 50 |  | 80 |  |  |
|  | 500 | 0 |  |  |
|  | 1000 | 0 |  |  |
| 50 | 500 | 98 | 90 | + |

EXAMPLE 39

Mixtures of (A) with Cyclosulfamuron (B39)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 6.25 and 12.5 g/ha and cyclosulfamuron at rates of 15 and 30 g/ha.

For some mixing ratios, a synergistic effect was observed with SCPJU, as shown in Table 39 below.

TABLE 39

| Dosage 1 (A) | Dosage 2 CyClosulfamuron | SCPJU activity (%) | Calculated using Colby's formula | Synergism |
|---|---|---|---|---|
| 6.25 |  | 30 |  |  |
| 12.5 |  | 50 |  |  |
|  | 15 | 60 |  |  |
|  | 30 | 90 |  |  |
| 12.5 | 15 | 80 | 80 | − |
| 6.25 | 30 | 100 | 93 | + |
| 12.5 | 30 | 100 | 95 | + |

EXAMPLE 40

Mixtures of (A) with Cyhalofop-butyl (B40)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 25 and 50 g/ha and cyhalofop-butyl at rates of 15 and 30 g/ha.

For some mixing ratios, a synergistic effect was observed with ECHCG, as shown in Table 40 below.

TABLE 40

| Dosage 1 (A) | Dosage 2 Pyributicarb | ECHCG activity (%) | Calculated using Colby's formula | Synergism |
|---|---|---|---|---|
| 25 |  | 30 |  |  |
| 50 |  | 80 |  |  |
|  | 15 | 50 |  |  |
|  | 30 | 80 |  |  |
| 25 | 15 | 80 | 65 | + |
| 50 | 15 | 95 | 90 | + |
| 25 | 30 | 90 | 86 | + |
| 50 | 30 | 98 | 96 | + |

EXAMPLE 41

Mixtures of (A) with NBA-061 (B41)

For the experiment, 1-(3-chloro-4,5,6,7-tetrahydropyrazolo-[1,5-a]-pyridin-2-yl)-5-(methylpropargylamino)-4-pyrazolylcarbonitrile (A) was applied at rates of 25 and 50 g/ha and NBA-061 at rates of 12.5 and 25 g/ha.

For some mixing ratios, a synergistic effect was observed with ECHCG, as shown in Table 41 below.

TABLE 41

| Dosage 1 (A) | Dosage 2 NBA-061 | ECHCG activity (%) | Calculated using Colby's formula | Synergism |
|---|---|---|---|---|
| 25 |  | 30 |  |  |
| 50 |  | 80 |  |  |
|  | 12.5 | 50 |  |  |
|  | 25 | 70 |  |  |
| 25 | 12.5 | 80 | 65 | + |
| 25 | 25 | 90 | 79 | + |
| 50 | 25 | 95 | 94 | + |

EXAMPLE 42

Mixtures of (A) with Azimsulfuron (B42)

For the experiment, 1-(3-chloro-4,5,6,7-tetrahydropyrazolo-[1,5-a]-pyridin-2-yl)-5-(methylpropargylamino)-4-pyrazolylcarbonitrile (A) was [lacuna] at rates of 30 and 60 g/ha and azimsulfuron at rates of 5 and 10 g/ha.

For some mixing ratios, a synergistic effect was observed with CYPSE, as shown in Table 42 below.

TABLE 42

| Dosage 1 (A) | Dosage 2 Pyributicarb | CYPSE activity (%) | Calculated using Colby's formula | Synergism |
|---|---|---|---|---|
| 30 |  | 50 |  |  |
| 60 |  | 70 |  |  |
|  | 5 | 70 |  |  |
|  | 10 | 80 |  |  |
| 30 | 10 | 100 | 90 | + |
| 60 | 10 | 100 | 94 | + |

We claim:

1. A synergistically active herbicidal composition which comprises, as active components, a mixture of 1-(3-chloro-4,5,6,7-tetrahydropyrazolo-[1,5-a]-pyridin-2-yl)-5-(methyipropargylamino)-4-pyrazolylcarbonitrile [Component (A)] and a herbicide selected from the group consisting of bentazone, molinate, daimuron, thiobencarb, butachlor, pretilachlor, dimepiperate, fenoxaprop-ethyl, clomeprop, cinmethylin, bromobutide, quinclorac, mefenacet, pyrazosulfuron-ethyl, esprocarb, cinosulfuron, thenylchlor, cumyluron, MK 243, naproanilide, anilofos, benfuresate, bifenox, CH-900, MCPA, nitrofen, oxadiazon, pendimethalin, simetryn, sulcotrione (ICIA0051), trifluralin, piperophos, pyributicarb, ethoxysulfuron, bensulfuronmethyl, pyrazolate, pyrazoxyfen, benzofenap, cyclosulfamuron, cyhalofop-butyl, NBA-061, azimsulfuron, propanil or imazosulfuron [Component (B)].

2. A herbicidal composition as claimed in claim 1 wherein the weight ratio of components (A) and (B) in the mixture is between 1:0.1 and 1:100.

3. A herbicidal composition as claimed in claim 2 wherein the weight ratio is between 1:0.5 and 1:50.

4. A method for controlling weeds, which comprises applying to the weeds or their locus an effective amount of a composition as claimed in claim 1.

5. The method as claimed in claim 4 wherein the weeds are controlled in a crop.

6. The method as claimed in claim 5, wherein the crop is rice.

* * * * *